United States Patent [19]
Von Strempel

[11] Patent Number: 6,117,136
[45] Date of Patent: Sep. 12, 2000

[54] HOOKS FOR IMPLANTS TO CORRECT AND STABILIZE THE VERTEBRAL COLUMN

[75] Inventor: Archibald Von Strempel, Burgwedel, Germany

[73] Assignee: Ulrich GmbH & Co. KG, Ulm, Germany

[21] Appl. No.: 09/269,613

[22] PCT Filed: May 20, 1998

[86] PCT No.: PCT/DE98/01437

§ 371 Date: Apr. 21, 1999

§ 102(e) Date: Apr. 21, 1999

[87] PCT Pub. No.: WO99/04716

PCT Pub. Date: Feb. 4, 1999

[30] Foreign Application Priority Data

Jul. 26, 1997 [DE] Germany .................. 197 32 187

[51] Int. Cl.[7] ............................................. A61B 17/56
[52] U.S. Cl. ............................................. 606/61; 606/72
[58] Field of Search ..................... 606/61, 69, 72, 606/73, 151

[56] References Cited

U.S. PATENT DOCUMENTS

| | | | |
|---|---|---|---|
| 4,611,582 | 9/1986 | Duff | 606/61 |
| 5,395,370 | 3/1995 | Muller et al. | 606/61 |
| 5,527,314 | 6/1996 | Brumfield . | |
| 5,928,231 | 7/1999 | Klein et al. | 606/61 |

FOREIGN PATENT DOCUMENTS

| | | |
|---|---|---|
| 0535623 | 4/1993 | European Pat. Off. . |
| 0571619 | 12/1993 | European Pat. Off. . |

*Primary Examiner*—Michael Buiz
*Assistant Examiner*—Julian W. Woo
*Attorney, Agent, or Firm*—Herbert Dubno Andrew Wilford

[57] ABSTRACT

A hook for implants for correcting and stabilizing the spinal column has a head (3) that has a seat (5) for a rod that can be inserted into and fixed on the head (3) and with a rear arm (4) hookable behind the bone. Two of the hooks are releasably latchable with each other at their heads (3) and have arms (4) that form a ring when latched together.

10 Claims, 2 Drawing Sheets

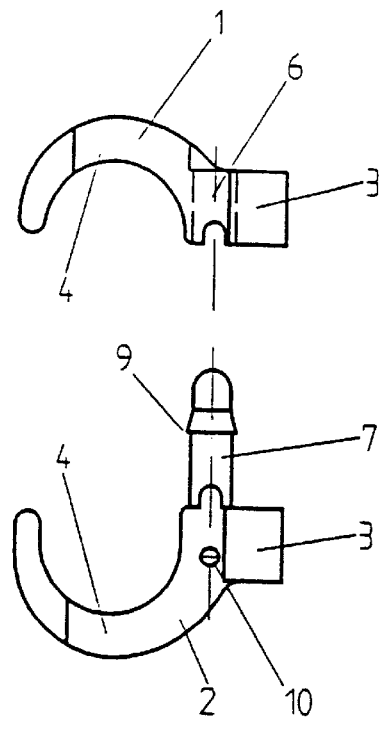
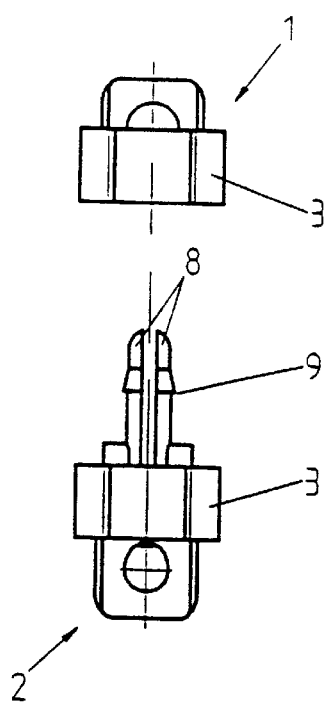
Fig. 1
Fig. 2
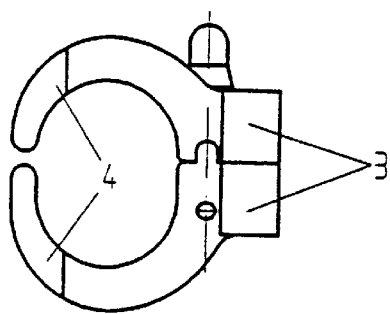
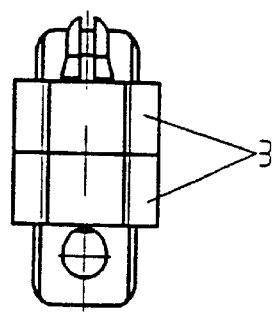
Fig. 3
Fig. 4

1

HOOKS FOR IMPLANTS TO CORRECT AND STABILIZE THE VERTEBRAL COLUMN

CROSS REFERENCE TO RELATED APPLICATIONS

This application is the US national phase of PCT application PCT/DE98/01437 filed May 20, 1998 with a claim to the priority of German application 197 32 187.8 filed Jul. 26, 1997.

FIELD OF THE INVENTION

The invention relates to a hook for implants for correcting and stabilizing the spinal column with a head that has a seat for a rod that can be inserted into and fixed on the head and with a rear arm hookable behind the bone.

BACKGROUND OF THE INVENTION

German 41 07 480 describes a pedicle screw which serves for anchoring implants in the spinal column to which end bores are formed in the pedicle of the vertebra in which the threaded shaft of a pedicle screw is threaded. This type of mounting of implants has shown itself effective in practice; however cases are known in which anatomical considerations exclude the use of a pedicle screw, for instance with anomalies or with such bone structures that do not allow the use of a screw.

It is known to use, as an alternative to a pedicle screw, hooks that are hung on the pedicle or on the lamina of the spinal column in order to effect a distraction or compression. Since the hooks are only secured at one arm, the result is in many cases an insecure mounting.

OBJECTS OF THE INVENTION

It is therefore an object of the invention to provide a hook of the above-described type which has an improved hold on the column.

SUMMARY OF THE INVENTION

This object is achieved in the above-described hook in that two of the hooks are provided whose heads are releasably latched to each other and whose arms form when latched together a ring.

The invention has the advantage that the column is surrounded by the latched-together ring-forming arms of the two hooks like a clamp. Thus there is not just a one-sided mounting of one of the hooks on the column which can be undone by a corresponding one-sided force, but the column is surrounded so that pressure and tensile forces can be transmitted.

To form the latch connection a bore is formed in the head of the first hook in which a pin formed on the head of the second hook can engage.

It is particularly preferable when the pin has a barb that in latched condition engages an undercut of the head of the first hook. Such hooking together produces a secure connection of the first hook with the second hook so that an unintentional or accidental separation of the two hooks is impossible.

In order to facilitate an intentional disconnection of the first hook from the second hook the pin is split and is formed of two spring tongues on which the barb is formed. The two spring tongues can be deflected so that the barbs are freed of the undercut and the pin can be pulled out of the bore of the first hook so that an emplaced hook can be moved around before the implant is finally positioned.

According to an alternative embodiment the pin is seated in a bore of the head of the second hook and is secured there by a pin inserted in a transverse bore. In addition to manufacturing advantages this embodiment has the additional advantage that after the pin is inserted into the bore of the first hook after the pin is withdrawn from the transverse bore it is also possible to separate the first hook from the second hook by driving the pin in the insert direction further through the bore of the first hook.

A particularly advantageous embodiment of the invention is characterized in that the head has a bow part reaching over both sides of the seat for the rod and having lateral arm parts releasably held on the head, and that presettable retaining parts are provided on the head and/or on the bow engageable against the rod in the recess to secure it by means of the bow closed over the recess to prevent it from shifting longitudinally. As a result of this construction the hooks can be used in standard implants with the extra step of first fitting the spinal column with the hooks and only subsequently setting the rod in place which makes manipulating the implant substantially easier.

The invention is further described in the following with reference to the embodiments shown in the drawing; therein

BRIEF DESCRIPTION OF THE DRAWINGS

FIG. 1 is a side view of first and second hooks before being joined together;

FIG. 2 is a top view of the structure of FIG. 1;

FIG. 3 is a view like FIG. 1 but with the hooks joined;

FIG. 4 is a view like FIG. 2 after joining;

SPECIFIC DESCRIPTION

Figure 5:
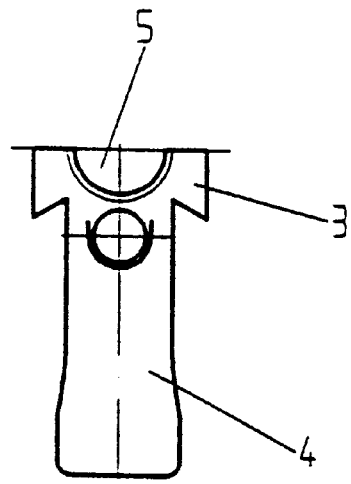
FIG. 5 is an end view of the second hook.

The hooks shown in the drawing are part of an unillustrated implant for correcting and stabilizing a spinal column. FIG. 1 shows at reference 1 a first hook and at reference 2 a second hook. The first hook 1 and the second hook 2 each have a head 3 and an arm 4. The head 3 is formed with a seat 5 in which a rod of the implant can be set and fixed. The first hook 1 and the second hook 2 can be latched together so that the arms 4 form a ring that engages around a vertebra like a clamp. In order to form the latch the head 3 of the first hook 1 has a bore 6 in which a pin 7 formed on the head 3 of the second hook 2 can engage, in the illustrated embodiment the pin 7 being formed of two elastic tongues on whose free ends barbs 9 are formed that engage an undercut when inserted in the bore 6 of the first hook. This formation as two spring tongues makes it possible to release the barb 9 from the undercut and separate the first hook 1 and the second hook 2 so that the position of the hook on the spinal column can be corrected.

Figure 6:
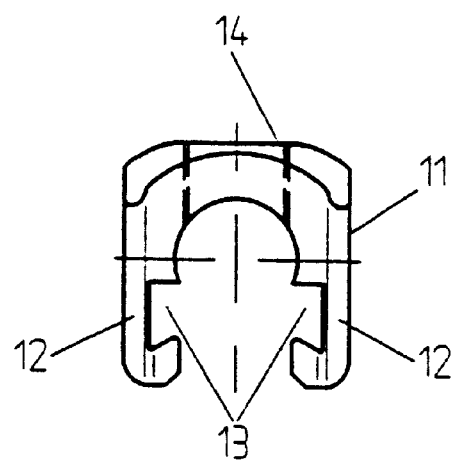
FIG. 6 is an end view of the bow part.

In the embodiment of FIGS. 1 to 4 the pin 7 is seated in a bore 6 of the head 3 of the second hook 2 and secured in place there by a pin 10 inserted in a transverse bore; in the embodiment of FIGS. 5 and 6 the pin 9 is one piece with the second hook 2.

German 41 07 480 shows how it is possible like with a pedicle screw to have a particularly advantageous connection on the rod of the implant with a hook having a similarly formed head. The hook according to the invention can be used in place of the pedicle screw of German 41 07 480 and thus forms part of an implant system where it is simple to secure the rod in the seat 5 of the head 3. With respect to the features resulting from the shape of the head 3 reference can be made to German 41 07 480 in which the features regarding the merits of the hook can also apply here. It is significant with this securing of the rod on the head 3 that a bow part 11 be provided that engages on both sides over the seat 5 for the rod and that has lateral arm parts that are guided by dove-tail formations 13 on the head 3. The bow part 11 has in a threaded hole 14 a clamping screw that can be advanced against the rod 15 formed as a threaded rod so that it presses with its screwthread against transverse ribs on the head 3.

What is claimed is:

1. A hook assembly for implants for correcting and stabilizing the spinal column with a head that has a seat for a rod that can be inserted into and fixed on the head and with a rear arm hookable behind the bone wherein the assembly comprises separate first and second hooks whose heads are releasably latchable with each other and whose arms form a ring when latched together, the first hook being formed with a bore and the second hook being formed with a pin longitudinally slidable in the bore;

the pin including elastic formations for releasably locking the first hook to the second hook.

2. A hook assembly for implants for correcting and stabilizing the spinal column with a head that has a seat for a rod that can be inserted into and fixed on the head and with a rear arm hookable behind the bone wherein the assembly comprises separate first and second hooks whose heads are releasably latchable with each other and whose arms form a ring when latched together, the first hook being formed with a bore and the second hook being formed with a pin longitudinally slidable in the bore; and a barb on the pin, the barb in a latched condition engaging an undercut of the head of the first hook for locking the first hook to the second hook.

3. The hook assembly according to claim 2 wherein the pin is split and is formed of two spring tongues on which the barb is formed.

4. The hook assembly according to claim 1 wherein the pin is seated in a bore of the head of the second hook and is secured there by a pin inserted in a transverse bore.

5. The hook assembly according to claim 1 wherein the head has a bow part reaching over both sides of the seat for the rod and having lateral arm parts releasably held on the head, and that presettable retaining parts are provided on the head engageable against the rod in the recess to secure it by means of the bow closed over the recess to prevent it from shifting longitudinally.

6. The hook assembly according to claim 5 wherein the lateral arm parts are guided by dove-tail formations on the head.

7. A hook assembly for an implant for correcting and stabilizing a spinal column, the assembly comprising:

a pair of hooks each having an arcuate arm, one of the hooks being formed with a bore and the other of the hooks provided with an unthreaded pin engageable and longitudinally slidable in the bore, the arms forming a ring when the pin is engaged in the bore, the hooks forming a head having a seat for a rod; and means for fixing the pin in the bore and for fixing the two hooks relative to each other.

8. The hook assembly defined in claim 7 wherein the fixing means includes a barb formed on the pin and engageable with the other hook.

9. The hook assembly defined in claim 8 wherein the pin is split longitudinally.

10. The hook assembly defined in claim 7 wherein the other hook is provided with a removable retaining pin securing the unthreaded pin in place in the other hook.

* * * * *